(12) United States Patent
Addison et al.

(10) Patent No.: US 9,955,894 B2
(45) Date of Patent: May 1, 2018

(54) NON-STATIONARY FEATURE RELATIONSHIP PARAMETERS FOR AWARENESS MONITORING

(71) Applicant: Covidien LP, Mansfield, MA (US)

(72) Inventors: Paul S. Addison, Edinburgh (GB); James N. Watson, Dunfermline (GB)

(73) Assignee: Covidien LP, Mansfield, MA (US)

( * ) Notice: Subject to any disclaimer, the term of this patent is extended or adjusted under 35 U.S.C. 154(b) by 594 days.

(21) Appl. No.: 14/606,943

(22) Filed: Jan. 27, 2015

(65) Prior Publication Data

US 2015/0208940 A1 Jul. 30, 2015

Related U.S. Application Data

(60) Provisional application No. 61/932,678, filed on Jan. 28, 2014.

(51) Int. Cl.
  *A61B 5/04* (2006.01)
  *A61B 5/0476* (2006.01)
  *A61B 5/00* (2006.01)

(52) U.S. Cl.
  CPC .......... *A61B 5/0476* (2013.01); *A61B 5/4821* (2013.01); *A61B 5/726* (2013.01)

(58) Field of Classification Search
  CPC ...... A61B 5/0476; A61B 5/4821; A61B 5/726
  See application file for complete search history.

(56) References Cited

U.S. PATENT DOCUMENTS

| | | |
|---|---|---|
| 4,289,141 A | 9/1981 | Cormier |
| 5,439,483 A | 8/1995 | Duong-Van |

(Continued)

FOREIGN PATENT DOCUMENTS

| | | |
|---|---|---|
| JP | 03-136408 | 6/1991 |
| JP | 09-084776 | 3/1997 |

(Continued)

OTHER PUBLICATIONS

Shen, Minfen, et al. "Novel approach for time-varying bispectral analysis of non-stationary eeg signals." Engineering in Medicine and Biology Society, 2005. IEEE-EMBS 2005. 27th Annual International Conference of the. IEEE, 2006.*

(Continued)

*Primary Examiner* — Navin Natnithithadha
*Assistant Examiner* — Andrey Shostak

(57) ABSTRACT

Methods and systems are presented for determining physiological information in a physiological monitor. A physiological signal (e.g., an EEG signal) received from a subject is wavelet transformed and first and second related features that vary in scale over time are identified in the transformed signal. First and second coupled ridges of the respective first and second related features may also be identified in the transformed signal. A non-stationary relationship parameter is determined and is indicative of the relationship between the first and second features and/or between the first and second ridges. Physiological information, which may be indicative of a level of awareness of a subject, is determined based on the non-stationary relationship parameter. This physiological information may be used, for example, in an operating room to monitor/regulate the subject's anesthetic state while under general anesthesia or in an intensive care unit to monitor the subject's sedateness and administer medication accordingly.

17 Claims, 8 Drawing Sheets

(56) References Cited

U.S. PATENT DOCUMENTS

| | | | |
|---|---|---|---|
| 5,458,117 A * | 10/1995 | Chamoun | A61B 5/048 600/547 |
| 5,590,650 A | 1/1997 | Genova | |
| 5,601,090 A | 2/1997 | Musha et al. | |
| 5,632,272 A | 5/1997 | Diab et al. | |
| 5,778,881 A | 7/1998 | Sun et al. | |
| 5,795,304 A | 8/1998 | Sun et al. | |
| 5,797,840 A | 8/1998 | Akselrod | |
| 5,827,195 A | 10/1998 | Lander | |
| 5,967,995 A | 10/1999 | Shusterman et al. | |
| 6,002,952 A | 12/1999 | Diab et al. | |
| 6,036,653 A | 3/2000 | Baba et al. | |
| 6,094,592 A | 7/2000 | Yorkey | |
| 6,095,984 A | 8/2000 | Amano et al. | |
| 6,117,075 A | 9/2000 | Barnea | |
| 6,129,675 A | 10/2000 | Jay | |
| 6,135,966 A | 10/2000 | Ko | |
| 6,171,257 B1 | 1/2001 | Weil et al. | |
| 6,171,258 B1 | 1/2001 | Karakasoglu et al. | |
| 6,208,951 B1 | 3/2001 | Kumar et al. | |
| 6,293,915 B1 | 9/2001 | Amano et al. | |
| 6,325,761 B1 | 12/2001 | Jay | |
| 6,361,501 B1 | 3/2002 | Amano et al. | |
| 6,393,311 B1 | 5/2002 | Edgar, Jr. et al. | |
| 6,561,986 B2 | 5/2003 | Baura | |
| 6,608,934 B2 | 8/2003 | Scheirer | |
| 6,654,623 B1 | 11/2003 | Kastle | |
| 6,654,632 B2 | 11/2003 | Lange et al. | |
| 6,731,975 B1 | 5/2004 | Viertio-Oja et al. | |
| 6,751,499 B2 | 6/2004 | Lange et al. | |
| 6,757,558 B2 | 6/2004 | Lange et al. | |
| 6,801,803 B2 | 10/2004 | Viertio-Oia et al. | |
| 6,810,277 B2 | 10/2004 | Edgar, Jr. et al. | |
| 6,826,426 B2 | 11/2004 | Lange et al. | |
| 6,931,269 B2 | 8/2005 | Terry | |
| 6,934,579 B2 | 8/2005 | Mantzaridis et al. | |
| 7,001,337 B2 | 2/2006 | Dekker | |
| 7,020,507 B2 | 3/2006 | Scharf | |
| 7,035,679 B2 | 4/2006 | Addison | |
| 7,043,293 B1 | 5/2006 | Baura | |
| 7,054,453 B2 | 5/2006 | Causevic | |
| 7,054,454 B2 | 5/2006 | Causevic et al. | |
| 7,079,888 B2 | 7/2006 | Oung | |
| 7,171,269 B1 | 1/2007 | Addison | |
| 7,173,525 B2 | 2/2007 | Albert | |
| 7,203,267 B2 | 4/2007 | De Man et al. | |
| 7,215,994 B2 | 5/2007 | Huiku | |
| 7,225,013 B2 | 5/2007 | Gera et al. | |
| 7,254,500 B2 | 8/2007 | Makeig | |
| 7,289,835 B2 | 10/2007 | Mansfield | |
| 7,367,949 B2 | 5/2008 | Korhonen et al. | |
| 7,515,949 B2 | 4/2009 | Norris | |
| 7,519,488 B2 | 4/2009 | Fu | |
| 7,523,011 B2 | 4/2009 | Akiyama et al. | |
| 2003/0163057 A1 | 8/2003 | Flick et al. | |
| 2004/0111033 A1 * | 6/2004 | Oung | A61B 5/02405 600/483 |
| 2005/0043616 A1 | 2/2005 | Chinchoy | |
| 2005/0143665 A1 | 6/2005 | Huiku et al. | |
| 2006/0004296 A1 | 1/2006 | Huiku et al. | |
| 2006/0209631 A1 | 9/2006 | Melese et al. | |
| 2006/0211930 A1 | 9/2006 | Scharf et al. | |
| 2006/0217614 A1 | 9/2006 | Takala et al. | |
| 2006/0217628 A1 | 9/2006 | Huiku | |
| 2006/0229519 A1 | 10/2006 | Fujiwara et al. | |
| 2006/0258921 A1 | 11/2006 | Addison et al. | |
| 2006/0265022 A1 | 11/2006 | John et al. | |
| 2007/0010723 A1 | 1/2007 | Utela et al. | |
| 2007/0021673 A1 | 1/2007 | Arbel et al. | |
| 2007/0073120 A1 | 3/2007 | Li et al. | |
| 2007/0073124 A1 | 3/2007 | Li et al. | |
| 2007/0167694 A1 | 7/2007 | Causevic et al. | |
| 2007/0167851 A1 | 7/2007 | Vitali et al. | |
| 2007/0282212 A1 | 12/2007 | Sierra et al. | |
| 2008/0045832 A1 | 2/2008 | McGrath | |
| 2008/0082018 A1 | 4/2008 | Sackner et al. | |
| 2008/0167540 A1 | 7/2008 | Korhonen et al. | |
| 2008/0214903 A1 | 9/2008 | Orbach | |
| 2008/0243021 A1 | 10/2008 | Causevic et al. | |
| 2010/0014761 A1 * | 1/2010 | Addison | A61B 5/14551 382/207 |
| 2011/0245709 A1 | 10/2011 | Greenwald | |

FOREIGN PATENT DOCUMENTS

| | | |
|---|---|---|
| WO | WO 01/025802 | 4/2001 |
| WO | WO 01/062152 | 8/2001 |
| WO | WO 03/055395 | 7/2003 |
| WO | WO 03/084396 | 10/2003 |
| WO | WO 04/105601 | 12/2004 |
| WO | WO 05/096170 | 10/2005 |
| WO | WO 06/085120 | 8/2006 |

OTHER PUBLICATIONS

Rampil, "A Primer for EEG Signal Processing in Anesthesia," Anesthesiology, vol. 89, 1998, pp. 980-1002.

Van Milligen et al., "Nonlinear Phenomena and Intermittency in Plasma Turbulence," Physical Review Letters, vol. 74, No. 3, Jan. 1995, pp. 395-398.

Bloom, M., et al., "Analgesics Decrease Arousal Response to Stimulation as Measured by Changes in Bispectral Index (BIS)," Anesthesiology 1996; 85(3A):A481.

Bloom,. M. et al., "BIS Variability Reflects Analgesia," J. Neurosurg. Anesthesiol. 2005; 17(4): 254-5.

Duggleby, W., et al., "Cognitive Status and Postoperative Pain: Older Adults," J. Pain. Symptom Manage 1994; 9:19-27.

Gan TJ. et al., "Bispectral Index Monitoring Allows Faster Emergence and Improved Recovery From Propofol, Alfentanil, and Nitrous Oxide Anesthesia," Anesthesiology 1997; 8494): 808-15.

Guignard B. et al., "The Effect of Remifentanil on the Bispectral Index Change and Hemodynamic Responses After Orotracheal Intubation," Anesth. Analg. 2000; 90(1): 161-7.

Iselin-chaves IA et al., "The Effect of the Interaction of Propofol and Alfentanil on Recall, Loss of Consciousness, and the Bispectral Index," Anesth. Analg. 1998; 87(4):949-55.

Jopling MW. et al., "Changes in the Bispectral Index (BIS) in the Presence of Surgical Stimulation Reflect the Level of Analgesia," Anesthesiology 1996; 85(3A); A478.

Kreuer, et al., "Comparison of Alaris AEP Index and Bispectral Index During Propofol-Remifentanil Anaesthesia," British Journal of Anaesthesia 91 (3): 336-340,2003.

Lynch, EPMD., et al. "The Impact of Postoperative Pain on the Development of Postoperative Delirium," Anest. & Analg. 1998; 86(4):781-5.

Monk TG, et al., "Anesthetic Management and One-Year Mortality After Noncardiac Surgery," Anesth. Analg. 2005; 100:4-10.

Morrison, RS, et al., "Relationship Between Pain and Opioid Analgesics on the Development of Delirium Following Hip Fracture," J. Gerontol. A. Biol. Sci. Med. Sci. 2003; 58:76-81.

Paravicini, et al., English Abstract of "Tramadol infusion anesthesia with the substitution of enflurane and various nitrous oxide concentrations," Database Medline, DN PubMed ID: 3919607 (Der Anaesthesist, (Jan. 1985) vol. 34, No. 1).

Schneider, et al., "Quality of Perioperative AEP-Variability of Expert Ratings," British Journal of Anaesthesia, 91 (6), 905-8 (2003).

Xie Z., et al., "The Inhalation Anesthetic Isoflurane Induces a Vicious Cycle of Apoptosis and Amyloid B-Protein Accumulation," J. Neurosci. 2007; 27:1247-1254.

* cited by examiner

NON-STATIONARY FEATURE RELATIONSHIP PARAMETERS FOR AWARENESS MONITORING

CROSS REFERENCE TO RELATED APPLICATION

This application claims the benefit of U.S. Provisional Application No. 61/932,678, filed Jan. 28, 2014, which is hereby incorporated by reference herein in its entirety.

SUMMARY

The present disclosure relates to monitoring a level of awareness of a subject with a physiological monitor, and more particularly, relates to computing non-stationary relationship parameters using a physiological monitoring system.

Methods and systems are provided for determining physiological information. In some embodiments, the system of the present disclosure may be physiological monitoring system such as an electroencephalograph (EEG) monitoring system. In some embodiments, the system receives a physiological signal from a subject, for example, an EEG signal, transforms the physiological signal using a wavelet transform, and identifies related, time-varying features in the resultant transformed signal. The system may determine a non-stationary relationship parameter based on the features, which is indicative of a relationship between the features. The system may use the non-stationary relationship parameter to determine physiological information, which may be indicative of a level of awareness of the subject.

In some embodiments, a system for determining physiological information includes an input configured for receiving a physiological signal from a subject. The system further includes one or more processors configured for transforming the physiological signal based on a wavelet transform to generate a transformed signal that comprises at least a time component and a scale component. The one or more processors are further configured for identifying a first feature and a second feature associated with the transformed signal that vary in scale over time, where the first feature is related to the second feature. The one or more processors are further configured for determining a non-stationary relationship parameter over time based on a third or higher order equation, the first feature, and the second feature, where the non-stationary relationship parameter is indicative of the relationship between the first feature and the second feature. The one or more processors are further configured for determining physiological information based on the non-stationary relationship parameter.

In some embodiments, a method for determining physiological information includes receiving a physiological signal from a subject and transforming the physiological signal based on a wavelet transform to generate a transformed signal that comprises at least a time component and a scale component. The method further includes identifying a first feature and a second feature associated with the transformed signal that vary in scale over time, where the first feature is related to the second feature. The method further includes determining a non-stationary relationship parameter over time based on a third or higher order equation, the first feature, and the second feature, where the non-stationary relationship parameter is indicative of the relationship between the first feature and the second feature. The method further includes determining physiological information based on the non-stationary relationship parameter.

BRIEF DESCRIPTION OF THE FIGURES

The above and other features of the present disclosure, its nature and various advantages will be more apparent upon consideration of the following detailed description, taken in conjunction with the accompanying drawings in which.

DETAILED DESCRIPTION OF THE FIGURES

Figure 1:
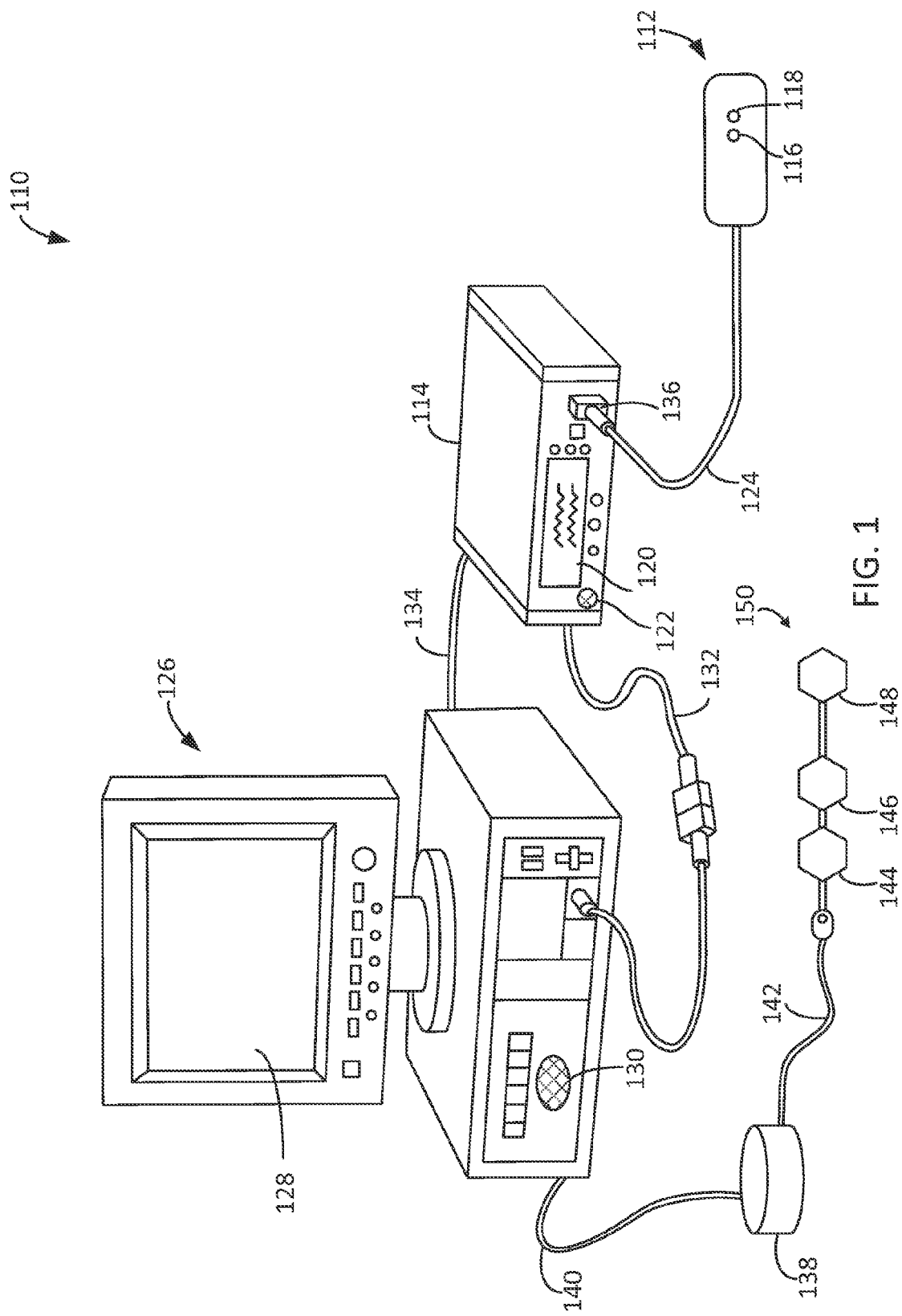
FIG. 1 is a perspective view of an illustrative physiological monitoring system in accordance with some embodiments of the present disclosure.

The present disclosure is directed towards methods and systems for determining physiological information from a physiological signal (e.g., an EEG signal) received from a subject. Processing equipment may transform the physiological signal using a wavelet transform to generate a transformed signal. The processing equipment may identify first and second features associated with the transformed signal. The first and second features may vary in scale over time. The processing equipment may determine values of a non-stationary relationship parameter indicative of the relationship between the first and second features (e.g., a measure of bicoherence) based on the first and second features and a third or higher order equation. The processing equipment may determine physiological information (e.g., a Synch-Fast-Slow Parameter) based on the non-stationary relationship parameter values. The determined physiological information may be indicative of a level of awareness of the subject. This physiological information may be used, for example, in an operating room setting to monitor and regulate the subject's anesthetic state while under general anesthesia during a surgical procedure or in an intensive care unit setting to monitor the subject's sedateness and administer medication accordingly.

In some embodiments, determining physiological information may include monitoring a level of awareness of a subject. It will be understood that level of awareness, as used herein, includes any measure indicative of a depth of consciousness, depth of sedateness, depth of anesthesia, awareness, any other suitable measure indicative of the subject's level of awareness, or any combination thereof. In monitoring the level of awareness of a subject, the processing equipment may determine non-stationary relationship parameters based on one or more of the subject's electrophysiological signals, such as EEG signals, electromyogram (EMG) signals, and/or electrooculogram (EOG) signals. In some embodiments, the processing equipment may process one or more of the electrophysiological signals to determine a consciousness index, which is indicative of a subject's depth of consciousness on a scale. For example, the bispectral (BIS) index is a processed parameter which may be derived utilizing a composite of measures from the EEG and physiological signal processing techniques including bispectral analysis, power spectral analysis, and time domain analysis. The BIS algorithm may be based at least in part on EEG signal features (bispectral and others) which may be highly correlated with sedation and/or hypnosis, including the degree of high frequency (14 to 30 Hz) activation, the amount of low frequency synchronization, the presence of nearly suppressed periods within the EEG, and the presence of fully suppressed (i.e., isoelectric, "flat line") periods within an EEG. The BIS index may provide an indication of a subject's depth of consciousness, with an index value of 0 representing a "flat line" EEG and an index value of 100 indicating a fully awake subject. Non-stationary relationship parameters indicative of a subject's level of awareness may be used by clinical care providers in operating room settings (e.g., in monitoring the subject's depth of anesthesia) or intensive care settings (e.g., in monitoring the subject's depth of sedateness) to evaluate a subject's status and provide treatment accordingly (e.g., adjusting anesthetic or analgesic administration).

FIG. 1 is a perspective view of an illustrative physiological monitoring system 110 in accordance with some embodiments of the present disclosure. In some embodiments, physiological monitoring system 110 may be implemented as part of an EEG monitoring system. In some embodiments, physiological monitoring system 110 may be implemented as part of a depth of consciousness or awareness monitoring system. In some embodiments, physiological monitoring system 110 may include sensor unit 112 and monitor 114. In some embodiments, sensor unit 112 may be part of an oximeter. Sensor unit 112 may include one or more light source 116 for emitting light at one or more wavelengths into a subject's tissue. One or more detector 118 may also be provided in sensor unit 112 for detecting the light that is reflected by or has traveled through the subject's tissue. Any suitable configuration of light source 116 and detector 118 may be used. In an embodiment, sensor unit 112 may include multiple light sources and detectors, which may be spaced apart. Physiological monitoring system 110 may also include one or more additional sensor units (not shown) that may, for example, take the form of any of the embodiments described herein with reference to sensor unit 112. An additional sensor unit may be the same type of sensor unit as sensor unit 112, or a different sensor unit type than sensor unit 112 (e.g., a photoacoustic sensor). Multiple sensor units may be capable of being positioned at two different locations on a subject's body.

In some embodiments, emitter 116 and detector 118 may be on opposite sides of a digit such as a finger or toe, in which case the light that is emanating from the tissue has passed completely through the digit. In an embodiment, emitter 116 and detector 118 may be arranged so that light from emitter 116 penetrates the tissue and is reflected by the tissue into detector 118, such as a sensor designed to obtain pulse oximetry data from a subject's forehead. Sensor unit 112 may also be included in an array of one or more additional types of sensors (e.g., electrodes for sensing electrophysiological signals such as EEG, EMG and/or EOG signals). For example, sensor unit 112 may be included in a multi-sensor array configured to be located on a subject's head. Additional embodiments are described in detail below.

In some embodiments, sensor unit 112 may be connected to monitor 114 as shown. Sensor unit 112 may be powered by an internal power source, e.g., a battery (not shown). Sensor unit 112 may draw power from monitor 114. In another embodiment, the sensor may be wirelessly connected (not shown) to monitor 114. Monitor 114 may be configured to calculate physiological parameters based at least in part on data received from any sensor of any type (e.g., an EEG or EMG electrode). For example, monitor 114 may implement a derivation of one or more of a depth of consciousness measure (e.g., the BIS index), an awareness parameter, a non-stationary relationship parameter, a higher order statistical measure, or any combination therein, as described herein, to determine physiological information related to a subject's awareness level. Monitor 114 may be configured to calculate physiological parameters based at least in part on data relating to light emission and detection received from one or more sensor units such as sensor unit 112. For example, monitor 114 may be configured to determine pulse rate, respiration rate, respiration effort, blood pressure, blood oxygen saturation (e.g., arterial, venous, or both), hemoglobin concentration (e.g., oxygenated, deoxygenated, and/or total), any other suitable physiological parameters, or any combination thereof. In some embodiments, calculations may be performed on the sensor units or an intermediate device and the result of the calculations may be passed to monitor 114. Further, monitor 114 may include display 120 configured to display the physiological parameters or other information about the system. In the embodiment shown, monitor 114 may also include a speaker 122 to provide an audible sound that may be used in various other embodiments, such as for example, sounding an audible alarm in the event that a subject's physiological parameters are not within a predefined normal range. In some embodiments, physiological monitoring system 110 may include a stand-alone monitor in communication with the monitor 114 via a cable or a wireless network link.

In some embodiments, sensor unit 112 may be communicatively coupled to monitor 114 via a cable 124 at input or port 136. Cable 124 may include electronic conductors (e.g., wires for transmitting electronic signals from detector 118), optical fibers (e.g., multi-mode or single-mode fibers for transmitting emitted light from light source 116), any other suitable components, any suitable insulation or sheathing, or any combination thereof. In some embodiments, a wireless transmission device (not shown) or the like may be used instead of or in addition to cable 124. Monitor 114 may include a sensor interface configured to receive physiological signals from sensor unit 112, provide signals and power to sensor unit 112, or otherwise communicate with sensor unit 112. The sensor interface may include any suitable hardware, software, or both, which may be allow communication between monitor 114 and sensor unit 112.

In the illustrated embodiment, physiological monitoring system 110 includes a multi-parameter physiological monitor 126. The monitor 126 may include a cathode ray tube display, a flat panel display (as shown) such as a liquid crystal display (LCD) or a plasma display, or may include any other type of monitor now known or later developed. Multi-parameter physiological monitor 126 may be configured to calculate physiological parameters and to provide a display 128 for information from monitor 114 and from other medical monitoring devices or systems (not shown). For example, multi-parameter physiological monitor 126 may be configured to display information regarding a subject's level of awareness, and blood oxygen saturation (referred to as an "SpO$_2$" measurement) and/or pulse rate information generated by monitor 114. Multi-parameter physiological monitor 126 may include a speaker 130.

Monitor 114 may be communicatively coupled to multi-parameter physiological monitor 126 via a cable 132 or 134 that is coupled to a sensor input port or a digital communications port, respectively and/or may communicate wirelessly (not shown). In addition, monitor 114 and/or multi-parameter physiological monitor 126 may be coupled to a network to enable the sharing of information with servers or other workstations (not shown). Monitor 114 may be powered by a battery (not shown) or by a conventional power source such as a wall outlet.

As depicted in FIG. 1, multi-parameter physiological monitor 126 may be communicably coupled to electrophysiological sensor 150. This coupling may occur through monitor interface cable 140, which connects to processing module 138, which itself connects to electrophysiological sensor 150 via physiological information cable 142. Processing module 138 may perform any of a number of processing operations (e.g., those described below), and may be implemented as described herein with reference to monitor 114. For example, processing module 138 may be a BISx® module, which may be configured to identify characteristics of electrophysiological sensor 150 (e.g., sensor arrangement, usage history) and/or to deliver signals (in raw or processed form) from electrophysiological sensor 150 to multi-parameter physiological monitor 126. Electrophysiological sensor 150 may include one or more individual electrophysiological sensors (such as electrodes 144, 146, and 148), which may be positioned at one or more body sites on a subject. In an embodiment, multi-parameter physiological monitor 126 may display a physiologically-based parameter, such as a BIS index, based at least in part on a signal from electrophysiological sensor 150 over an interval of time and at a particular frequency, which may be adjusted by a user (e.g., the last 15 to 30 seconds, and updated every second).

In some embodiments, electrophysiological sensor 150 may be connected directly to multi-parameter physiological monitor 126, without the use of processing module 138. In an embodiment, processing module 138 may be included within multi-parameter physiological monitor 126. In an embodiment, both sensor 112 and electrophysiological sensor 150 may be communicably coupled to a common processing module (e.g., processing module 138) which may transmit information based on signals from one or more of the sensors to a monitoring device (e.g., multi-parameter physiological monitor 126). As described above, sensors 112 and 150 may be configured in a unitary sensor body, or may be physically attached to each other. In an embodiment, multi-parameter physiological monitor 126 and monitor 114 may be combined into a single monitoring device. It will be noted that any suitable configuration of sensing and monitoring devices adapted to perform the techniques described herein may be used.

Figure 2:
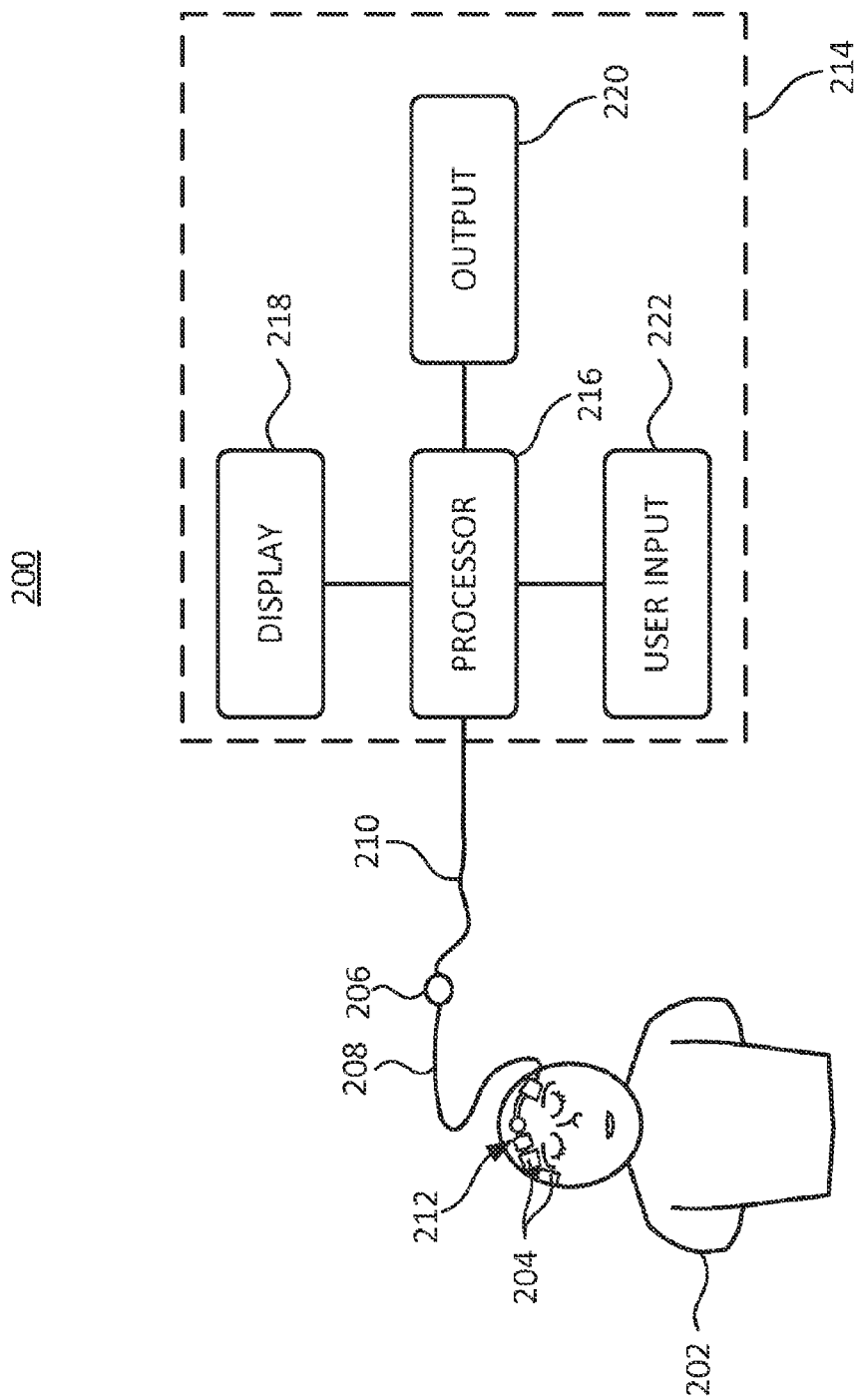
FIG. 2 is a block diagram of an illustrative physiological monitoring system in accordance with some embodiments of the present disclosure.

FIG. 2 is a block diagram of an illustrative physiological monitoring system 200 in accordance with some embodiments of the present disclosure. Physiological monitoring system 200 includes sensor unit 212, including one or more surface electrodes 204, which is communicatively coupled by cable 208 to processing module 206. Processing module 206 may be communicatively coupled by cable 210 to processing system 214. For example, cable 210 may be coupled to an input of processing system 214. In the illustrated embodiment, processing system 214 may include processor 216 coupled to display 218, output 220, and user input 222.

In some embodiments, sensor unit 212 may include EEG leads connected to the head of subject 202 by one or more surface electrodes 204, which, in some embodiments, are part of a BIS® 4 Electrode Sensor (Covidien LP, Mansfield, Mass.). In some embodiments, sensor unit 212 may detect and transmit EEG signals over cable 208 to processing module 206, which may generate and transmit an input signal, including information based on signals from sensor unit 212, over cable 210 to processing system 214. The signals generated by sensor unit 212 may be applied to any device used to process EEG signals. For example, sensor unit 212 may be applied to a Bispectral Index (BIS®) generator of the type disclosed in Chamoun et al. U.S. Pat. No. 5,458,117, issued Oct. 17, 1995, the entirety of which is incorporated by reference herein.

In some embodiments, processing module 206 may correspond to processing module 138 of FIG. 1. For example, processing module 206 may be a BISx® module, which may be configured to identify characteristics of sensor unit 212 (e.g., sensor arrangement, usage history) and/or to transmit an input signal over cable 210 to processing system 214. In some embodiments, the input signal may include signals (in raw or processed form) from sensor unit 212. The input signal may include, for example, an EEG signal generated in known fashion by one or more surface electrodes 204 of sensor unit 212. In some embodiments, processing module 206 may include an amplifier or other known EEG signal processing components, and the input signal transmitted over cable 210 may include signals generated by one or more of these components. In some embodiments, the input signal may be representative of cerebral activity of subject 202, and processing system 214 may receive the input signal and determine physiological information indicative of a level of awareness of subject 202. In some embodiments, sensor unit 212 may be connected directly to processing system 214, without the use of processing module 206. In some embodiments, processing module 206 may be included within processing system 214. It will be understood that any suitable configuration of sensing and monitoring devices adapted to perform the techniques described herein may be used.

Processor 216 of processing system 214 may be any suitable software, firmware, hardware, or combination thereof for processing the input signal. For example, processor 216 may include one or more hardware processors (e.g., integrated circuits), one or more software modules, non-transitory computer-readable media such as memory, firmware, or any combination thereof. In some embodiments, processor 216 may include a computer or one or more chips (i.e., integrated circuits). Processor 216 may, for example, include an assembly of analog electronic components. In some embodiments, processor 216 may determine physiological information associated with subject 202. For example, processor 216 may compute one or more of a BIS index value, higher order statistical measures, non-stationary relationship parameters, physiological information indicative of a level of awareness of subject 202, or any other suitable physiological parameter. Processor 216 may perform any suitable signal processing of the input signal to filter the input signal, such as any suitable band-pass filtering, adaptive filtering, closed-loop filtering, any other suitable filtering, and/or any combination thereof. Processor 216 may also receive input signals from additional sources (not shown). For example, processor 216 may receive an input signal containing information about treatments provided to the subject. Additional input signals may be used by processor 216 in any of the calculations or operations it performs in accordance with processing system 200. In some embodiments, processor 216 may be adapted to execute software, which may include an operating system and one or more applications, as part of performing the functions described herein. In some embodiments, processor 216 may include one or more processors for performing each or any combination of the functions described herein.

In some embodiments, processor 216 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. Any suitable computer-readable media may be used in the system for data storage. Computer-readable media are capable of storing information that can be interpreted by processor 216. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, writable and non-writable, and removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system. The computer storage media may be used by processor 216 to, for example, store fiducial information or initialization information corresponding to physiological monitoring. In some embodiments, processor 216 may store physiological measurements or previously received data from input signal 210 in a memory device for later retrieval. In some embodiments, processor 216 may store calculated values, such as BIS index values, non-stationary relationship parameters, higher order statistics, a level of awareness of subject 202, a fiducial point location or characteristic, an initialization parameter, or any other calculated values, in a memory device for later retrieval.

Processor 216 may be coupled to display 218, user input 222, and output 220. In some embodiments, display 218 may include one or more display devices (e.g., monitor, PDA, mobile phone, any other suitable display device, or any combination thereof). For example, display 218 may be configured to display physiological information determined by physiological monitoring system 200. In some embodiments, display 218 may correspond to display 120 or 128 of FIG. 1. In some embodiments, user input 222 may be used to enter information about the subject, such as age, weight, height, diagnosis, medications, treatments, and so forth. In some embodiments, display 218 may exhibit a list of values which may generally apply to the subject, such as, for example, age ranges or medication families, which the user may select using user input 222.

In some embodiments, output 220 may include one or more medical devices (e.g., a medical monitor that displays various physiological parameters, a medical alarm, or any other suitable medical device that either displays physiological parameters or uses the output of processor 216 as an input), one or more audio devices, one or more printing devices, any other suitable output device, or any combination thereof. For example, output 220 may generate a printed output of physiological information determined by physiological monitoring system 200. In some embodiments, output 220 may include a communications interface that may enable processing system 214 to exchange information with external devices. The communications interface may include any suitable hardware, software, or both, which may allow physiological monitoring system 200 (e.g., processing system 214) to communicate with electronic circuitry, a device, a network, or any combinations thereof. The communications interface may include one or more receivers, transmitters, transceivers, antennas, plug-in connectors, ports, communications buses, communications protocols, device identification protocols, any other suitable hardware or software, or any combination thereof. The communications interface may be configured to allow wired communication (e.g., using USB, RS-232, Ethernet, or other standards), wireless communication (e.g., using WiFi, IR, WiMax, BLUETOOTH, UWB, or other standards), or both. For example, the communications interface may be configured using a universal serial bus (USB) protocol (e.g., USB 2.0, USB 3.0), and may be configured to couple to other devices (e.g., remote memory devices storing templates) using a four-pin USB standard Type-A connector (e.g., plug and/or socket) and cable. In some embodiments, the communications interface may include an internal bus such as, for example, one or more slots for insertion of expansion cards.

It will be understood that physiological monitoring system 200 may be incorporated into physiological monitoring system 110 of FIG. 1. For example, sensor unit 212 may be implemented as part of sensor unit 150. Processing system 214 may be implemented as part of monitor 114 or multi-parameter physiological monitor 126 of FIG. 1. Display 218 may be implemented as display 120 or 128 of FIG. 1. Furthermore, all or part of physiological monitoring system 200 may be embedded in a small, compact object carried with or attached to subject 202 (e.g., a watch, other piece of jewelry, or a smart phone). In some embodiments, a wireless transceiver (not shown) may also be included in physiological monitoring system 200 to enable wireless communication with other components of physiological monitoring system 110 of FIG. 1. As such, physiological monitoring system 200 of FIG. 2 may be part of a fully portable and continuous subject monitoring solution. In some embodiments, a wireless transceiver (not shown) may also be included in physiological monitoring system 200 to enable wireless communication with other components of physiological monitoring system 110 of FIG. 1. For example, processing module 206 may communicate its generated input signal over BLUETOOTH, 802.11, WiFi, WiMax, cable, satellite, Infrared, or any other suitable transmission scheme. In some embodiments, a wireless transmission scheme may be used between any communicating components of physiological monitoring system 200. In some embodiments, physiological monitoring system 200 may include one or more communicatively coupled modules configured to perform particular tasks. In some embodiments, physiological monitoring system 200 may be included as a module communicatively coupled to one or more other modules.

It will be understood that the components of physiological monitoring system 200 that are shown and described as separate components are shown and described as such for illustrative purposes only. In other embodiments the functionality of some of the components may be combined in a single component. For example, the functionality of processor 216 and processing module 206 may combined in a single processor system. Additionally, the functionality of some of the components shown and described herein may be divided over multiple components. Additionally, physiological monitoring system 200 may perform the functionality of other components not show in FIG. 2. In some embodiments, the functionality of one or more of the components may not be required. In some embodiments, all of the components can be realized in processor circuitry.

In some embodiments, any of the processing components and/or circuits, or portions thereof, of FIGS. 1 and 2, including sensors 112, 150, and 212, monitors 114 and 126, processor 216, and processing system 214 may be referred to collectively as processing equipment. For example, processing equipment may be configured to amplify, filter, sample and digitize an input signal from sensors 112, 150, and 212 (e.g., using an analog-to-digital converter), determine physiological information and higher order statistical measures from the digitized signal, and display the physiological information. The processing equipment may include one or more processors. In some embodiments, all or some of the components of the processing equipment may be referred to as a processing module.

In some embodiments, the processing equipment may receive a physiological signal (e.g., an EEG signal), generate a transformed physiological signal, and compute higher-order statistical (HOS) measures based on the physiological signal to determine useful physiological information. HOS measures are useful in analyzing physiological signals, including non-Gaussian signals and signals with additive Gaussian noise, by detecting certain nonlinearities and extracting phase information. For purposes of brevity and clarity, and not by way of limitation, the received physiological signal is described in some embodiments as an EEG signal. It will be understood that the received physiological signal is not limited to an EEG signal and may correspond to EMG signals, electrocardiograms (ECG), electrogastrograms (EGG), PPG signals, optical light signals, pulse rate signals, pathological signals, ultrasound signals, pressure signals, impedance signals, temperature signals, acoustic signals, any other suitable electrophysiological signals, any other suitable biosignals, or any combination thereof.

In some embodiments, determining HOS measures may include performing a bispectral analysis on the transformed EEG signal. It will be understood that higher order statistics, as used herein, refers to third or higher order statistics. The order of a statistic is related to the moments, or expected values, which may be calculated for a signal (e.g., an EEG signal). The first order moment is the arithmetic mean of the signal; the second order is the variance; the third order is the skewness; and the fourth order is the kurtosis of the probability function. In spectral analysis, first order statistics include the mean and variance of the amplitude of the signal waveform. The second order statistics include the power spectrum, or in the time domain, the autocorrelation. Higher order statistics (i.e., third or higher) include the bispectrum, which is of the third order, and the trispectrum, which is of the fourth order. As noted above, the order of a statistic is related to the order of the relevant moment. For example, the bispectrum can be viewed as a decomposition of the third order moment (skewness) of a signal over frequency or scale. It will be understood that third and fourth order statistics are presented for illustration and not by means of limitation, and higher order statistics may correspond to statistics of a higher order than fourth. In some embodiments, the processing equipment may determine the bispectrum and bicoherence values, based on the transformed EEG signal. The bispectrum and bicoherence measures may be useful in determining a level of awareness of a subject (e.g., depth of anesthesia). The bispectrum includes both phase and power information and may quantify the relationship between related features of a transformed EEG signal. The bicoherence is a squared, normalized value of the bispectrum, and may be indicative of an amount of phase coupling between the related features.

Traditionally, HOS measures are computed based on a physiological signal that has been transformed using a Fourier transform. In the Fourier domain, bicoherence is calculated from the third order bispectrum measure, where the Fourier values at frequencies $f_1$, $f_2$, and $f_3$ are considered and $f_3=f_1+f_2$. Computation of these HOS measures from EEG signals in the Fourier domain is discussed in detail in Ira J. Rampil, "A Primer for EEG Signal Processing in Anesthesia," *Anesthesiology*, vol. 89, pp. 980-1002, 1998, which is incorporated by reference herein in its entirety.

Bispectrum and bicoherence measures may also be computed based on a wavelet transformed signal, as described with regard to fluid turbulence analysis in B. Ph. van Milligen, C. Hidalog, and E. Sánchez, "Nonlinear Phenomena and Intermittency in Plasma Turbulence," *Physical Review Letters*, vol. 74, no. 3, 16 Jan. 1995, which is incorporated by reference herein in its entirety. The method works by summing over time across three wavelet scales, $a_1$, $a_2$, and $a_3$, where the scales are related by:

$$\frac{1}{a_1} + \frac{1}{a_2} = \frac{1}{a_3} \quad [1]$$

The wavelet bispectrum for a signal is given by:

$$B^w(a_1, a_2) = \int_\tau T(a_1, b)T(a_2, b)T^*(a_3, b)db \quad [2]$$

The squared wavelet bicoherence measure for a signal is given by:

$$Bic^w(a_1, a_2)^2 = \frac{|B^w(a_1, a_2)|^2}{\int_\tau |T(a_1, b)T(a_2, b)|^2 db P^w(a_3)} \quad [3]$$
$$= \frac{\left|\int_\tau T(a_1, b)T(a_2, b)T^*(a_3, b)db\right|^2}{\int_\tau |T(a_1, b)T(a_2, b)|^2 db P^2(a_3)},$$

where T(a, b) is the wavelet transform of the signal, T*(a, b) denotes the complex conjugate of T(a, b), and $$P^W(a_3)=\int_\tau T^*(a_3,b) \cdot T(a_3,b)db \quad [4]$$

The wavelet bicoherence may be mapped onto the ($a_1$, $a_2$)-plane. The wavelet bicoherence may also be mapped onto the ($f_{c1}$, $f_{c2}$)-plane, where $f_{cx}$ is the characteristic frequency relating to the wavelet at scale $a_x$.

As with traditional Fourier-based, frequency domain techniques for determining HOS measures, the wavelet measures described above assume a stationarity over the integration timescale. Eqs. 2 and 3, above, for computing the bispectrum and bicoherence, respectively, include integrals that sum fixed a-scales over time τ. While these stationary wavelet bispectrum and bicoherence measures are advantageous, as compared to the traditional Fourier-derived measures, in that they smooth over the range of scales considered, the stationary wavelet measures are not capable of dynamically tracking related features of a transformed physiological signal in time and scale simultaneously. In other words, because the stationary wavelet measures are based on an assumption of fixed a-scales over the integration timescale τ, they cannot track related features that vary in scale over time.

The present disclosure provides methods and systems for determining, in the wavelet transform domain, non-stationary parameters indicative of relationships between time-varying features (i.e., features that vary in scale over time). These non-stationary relationship parameters are not based on an assumption of fixed a-scales and are thus able to track related, time-varying features in both scale and time.

In some embodiments, the processing equipment may determine non-stationary relationship parameter values based on a wavelet transformed physiological signal (e.g., an EEG signal). Non-stationary relationship parameters may include any measure indicative of a relationship between features of the wavelet transformed physiological signal, for example, HOS measures. In some embodiments, non-stationary relationship parameters may be determined based on a bispectral analysis (e.g., determining the bispectrum and/or bicoherence values) of a wavelet transformed EEG signal. In some embodiments, the bispectral analysis includes computation of instantaneous, non-stationary wavelet measures. In some embodiments, the processing equipment may identify wavelet scales $a_1$ and $a_2$ and a modulation component at scale $a_3$, where $a_1$, $a_2$, and $a_3$ satisfy Eq. 1 above (i.e., $a_1$ and $a_2$ correspond to related features). Each set of scales ($a_1$, $a_2$, $a_3$) is a triplet. In some embodiments, the processing equipment may determine an instantaneous non-stationary bispectrum value $I\_B(a_1, a_2)$ for each triplet ($a_1$, $a_2$, $a_3$). In some embodiments, the instantaneous non-stationary wavelet bispectrum (I_B) is given by:

$$I\_B(a_1,a_2)=T(a_1,b)\cdot T(a_2,b)\cdot T^*(a_3,b) \quad [5]$$

with magnitude:

$$|I\_B(a_1,a_2)|=|T(a_1,b)\cdot T(a_2,b)\cdot T^*(a_3,b)| \quad [6]$$

In some embodiments, the instantaneous non-stationary wavelet bicoherence (I_NSBic) is given by:

$$I\_NSBic(a_1, a_2, b) = \frac{|T(a_1, b)\cdot T(a_2, b)\cdot T^*(a_3, b)|}{\sqrt{|T(a_1, b)|^2 \cdot |T(a_2, b)|^2 \cdot |T^*(a_3, b)|^2}} \quad [7]$$

The processing equipment may determine values of the I_NSBic for each triplet ($a_1$, $a_2$, $a_3$) over time b (e.g., using Eq. 7).

Figure 3:
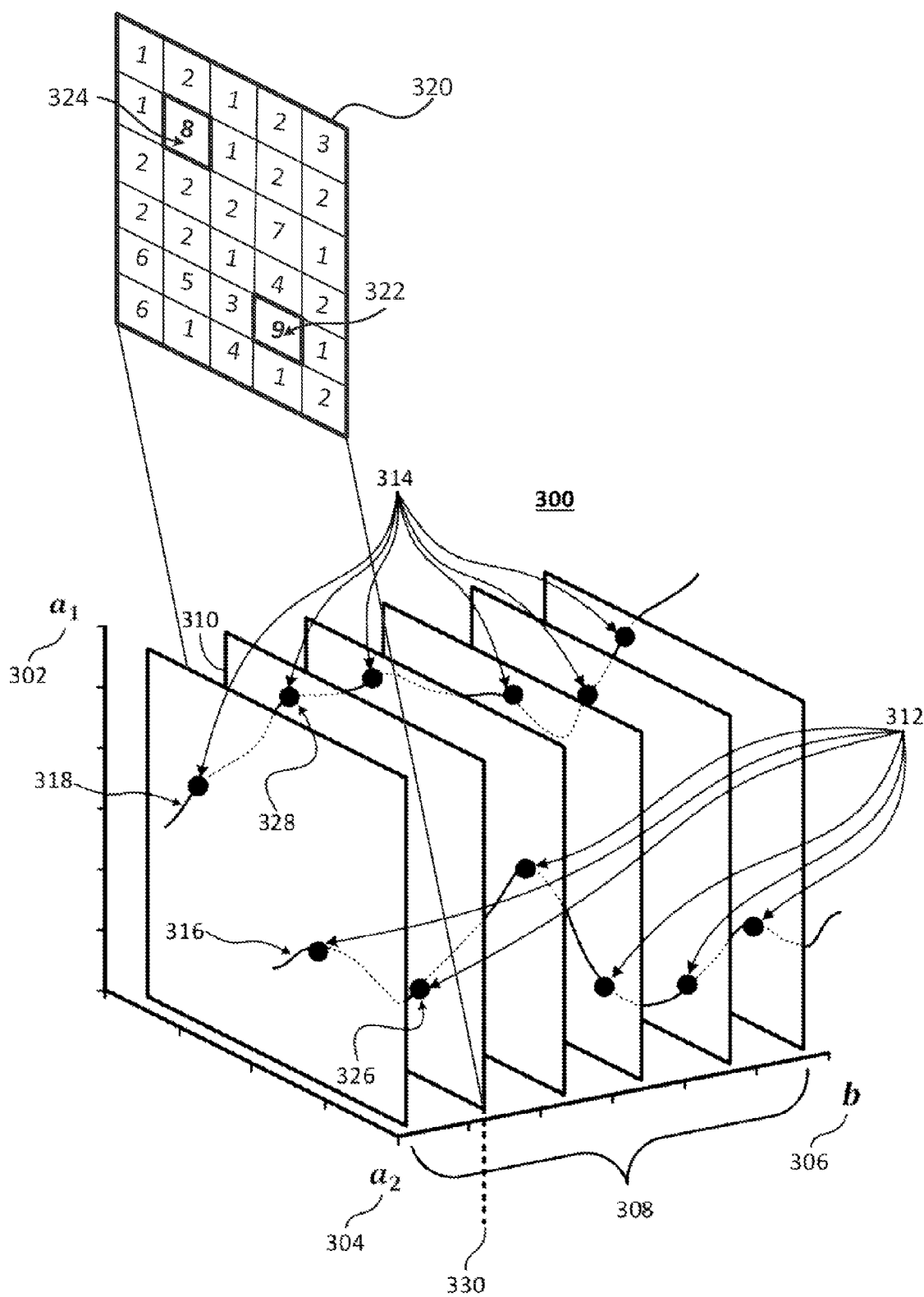
FIG. 3 is an illustrative plot of instantaneous, non-stationary relationship parameter values in accordance with some embodiments of the present disclosure.

FIG. 3 is an illustrative plot 300 of instantaneous, non-stationary relationship parameter values in accordance with some embodiments of the present disclosure. Plot 300 includes scale axes 302 and 304 corresponding to scales $a_1$ and $a_2$, respectively, and time axis 306, corresponding to time b, which form the $a_1$-$a_2$-b space. The $a_1$-$a_2$-b space of plot 300 includes a group of $a_1$-$a_2$ planes 308, each of planes 308 corresponding to values of a non-stationary relationship parameter for combinations of scales $a_1$ and $a_2$ at a particular time b. Planes 308 include $a_1$-$a_2$ plane 310. Planes 308 collectively form a three-dimensional volume of non-stationary relationship parameter values over time b. Points 312 and 314 correspond to the two highest local maxima in each of $a_1$-$a_2$ planes 308. Points 326 and 328 correspond to local maxima in $a_1$-$a_2$ plane 310. Threads 316 and 318 are shown connecting the local maxima of each plane 308 across time b. Two-dimensional plane 320 corresponds to $a_1$-$a_2$ plane 310, which is representative of values of the non-stationary relationship parameter at time 330. Plane 320 is presented as a two-dimensional grid of squares containing numerical values, each representative of an instantaneous value of a non-stationary relationship parameter for a particular combination of scales $a_1$ and $a_2$ at time 330. Shown in bold, local maxima 322 and 324 of plane 320 correspond to points 326 and 328, respectively, of plane 310.

In some embodiments, $a_1$-$a_2$ planes 308 may each represent the I_NSBic values for all permutations of scales $a_1$ and $a_2$ at a respective time b. Taken as a whole, planes 308 form a volume of I_NSBic values within the $a_1$-$a_2$-b space. Threads 316 and 318 are shown in the $a_1$-$a_2$-b space of plot 300 as connecting the local maxima I_NSBic values for each $a_1$-$a_2$ plane 308 across time b. In some embodiments, threads 316 and 318 correspond to I_NSBic triplets linked across time b. In some embodiments, threads 316 and 318 may correspond to a metric associated with related features of the transformed physiological signal over time b, including peak power, peak energy, I_B magnitude, any other suitable metric, or any combination thereof. The depiction in plot 300 of $a_1$-$a_2$ planes 308 through time b provides a clear illustration of the temporal aspect of relative phase couplings of related features within the EEG signal, shown as threads 316 and 318 in plot 300.

Determining the instantaneous non-stationary relationship parameters using any of the foregoing techniques may require analysis of the three-dimensional $a_1$-$a_2$-b space for areas of feature coupling or any other suitable relationship between features in the transformed signal (e.g., locating the local maxima points 312 and 314 corresponding to features coupling in each plane 308 across time b). Because this may be a computationally intensive analysis, it would be advantageous to reduce the search space of the analysis. In some embodiments, the processing equipment may determine non-stationary relationship parameters by identifying features (e.g., ridges) in the transformed signal and integrating only over the identified features over time, as opposed to integrating over all possible combinations of scales $a_1$ and $a_2$ for each time b and analyzing the entire three-dimensional $a_1$-$a_2$-b space, shown in plot 300, in order to identify related features of the transformed signal.

In some embodiments, the processing equipment may identify ridges of related features in the transformed signal. In some embodiments, ridges may correspond to the loci of maxima or minima values of the transformed signal across time. In some embodiments, ridges may correspond respectively to features of the transformed signal that vary in scale over time. In some embodiments, the processing equipment may identify coupled ridge pairs, which include first and second coupled ridges. Coupling may be a predictable feature in the wavelet transform space, although it may be unrelated to the wavelet transform itself. Coupling may be caused by the modulation of two dominant ridge scales of the signal, and the modulation may include a product in the time domain that may lead to a convolution of the two dominant ridge scales in the wavelet transform domain.

Coupling may include any relationship between ridges, features, and/or scales, including, for example, phase coupling, grouping, similar characteristic shapes, signature patterns, any other morphology characteristic, any other determinable relationship, or any combination thereof.

In some embodiments, the processing equipment may determine non-stationary relationship parameters based on identified ridges of features in the transformed signal. In some embodiments, the processing equipment may determine non-stationary relationship parameters based on identified coupled ridge pairs in the transformed signal. It will be understood that the transformed signal may correspond to any transformed signal, transformation of a transformed signal, rescaled version of a transformed signal, modulus of a transformed signal, phase of a transformed signal, squared magnitude of a transformed signal, any other suitable signal resulting from further signal processing or manipulation of the transformed signal, or any combination thereof. For example, the processing equipment may determine non-stationary relationship parameter values based on a rescaled, transformed signal, where the rescaling produces ridges in the transformed signal having amplitudes that scale with the amplitudes of the corresponding features in the original received signal. The processing equipment may determine a non-stationary relationship parameter based on the rescaled, transformed signal, by integrating along a ridge in the rescaled, transformed signal, and the non-stationary relationship parameter may be indicative of the total energy of the feature corresponding to the rescaled ridge. In addition, dividing the determined parameter by the integration time may yield a measure of the time-normalized energy (i.e., power) of the feature.

In some embodiments, the processing equipment may perform other operations on a feature or set of features in the transform space to determine certain characteristics or relationships that exist between them. Hence, rather than an instantaneous measure, a summed non-stationary Bicoherence measure (NSBic) may be generated for a set of features $F_1$ and $F_2$ through time. In some embodiments, the processing equipment may identify coupled ridges $R_1$ and $R_2$ and a modulation component at ridge $R_3$, where $R_1$ and $R_2$ form a coupled ridge pair and correspond respectively to related features $F_1$ and $F_2$. In some embodiments, NSBic is given by:

$$NSBic^w(F_1, F_2)^2 = \frac{\left|\int_\tau R_1(a,b)R_2(a,b)R_3^*(a,b)db\right|^2}{\int_\tau |R_1(a,b)R_2(a,b)|^2 db \int_\tau R_3(a,b)R_3^*(a,b)db} \quad [8]$$

where $R(a, b)$ is the set of transform values $T(a_R, b_R)$ along the ridge R, and $(a_R, b_R)$ are the scale and time values of the ridge R over the time segment $\tau$ being considered. Typically, $a_R$ is not constant and is a function of time. In some embodiments, the non-stationary bispectrum measure (NSB) is given by:

$$NSB^w(F_1, F_2) = \int_\tau R_1(a,b)R_2(a,b)R_3^*(a,b)db \quad [9]$$

As shown in Eqs. 8 and 9, these techniques for computing the NSBic and NSB, respectively, integrate along the ridges $R_1$, $R_2$, and $R_3$, as opposed to the techniques for computing the stationary parameters, which integrate along fixed scales, as shown in Eqs. 2. In some embodiments, the timescale of integration $\tau$ may be set at an appropriate period. For example, the timescale of integration $\tau$ may be set to the period of the longest of the three ridges $R_1$, $R_2$, and $R_3$. As another example, the timescale of integration $\tau$ may be set to the period of the shortest or middle size of ridges $R_1$, $R_2$, and $R_3$ or to a predetermine period of time. In some embodiments, the processing equipment may determine NSBic and NSB based on Eqs. 8 and 9, respectively, and the determined NSBic and NSB values may be used as markers of a subject's level of awareness. In some embodiments, the processing equipment may determine the NSBic for various regions of a set of features and compare the determined NSBic values to determine a degree of coherence displayed by the set of features over time.

Figure 4:
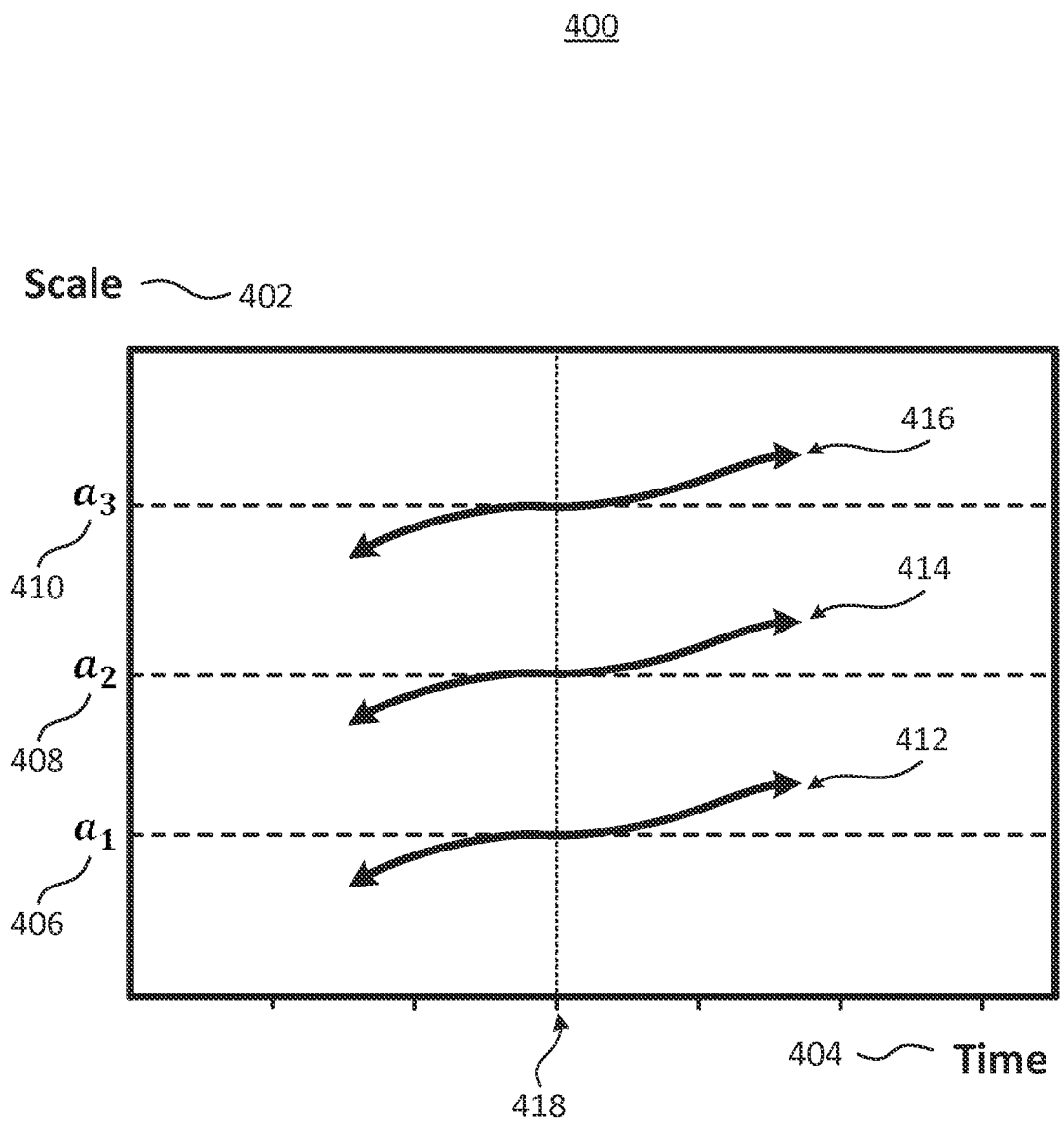
FIG. 4 is an illustrative plot for identifying coupled ridge pairs in accordance with some embodiments of the present disclosure.
Figure 5:
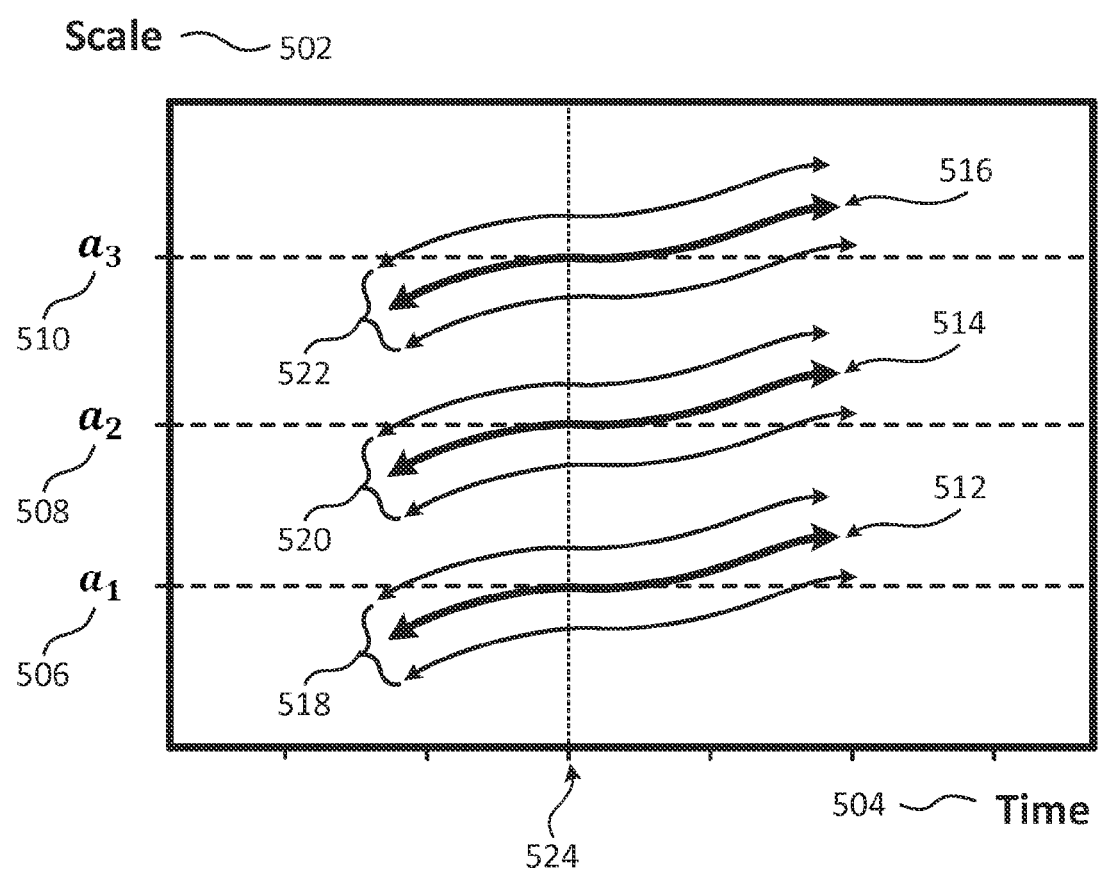
FIG. 5 is an illustrative plot for identifying coupled ridge pairs in accordance with some embodiments of the present disclosure.
Figure 6:
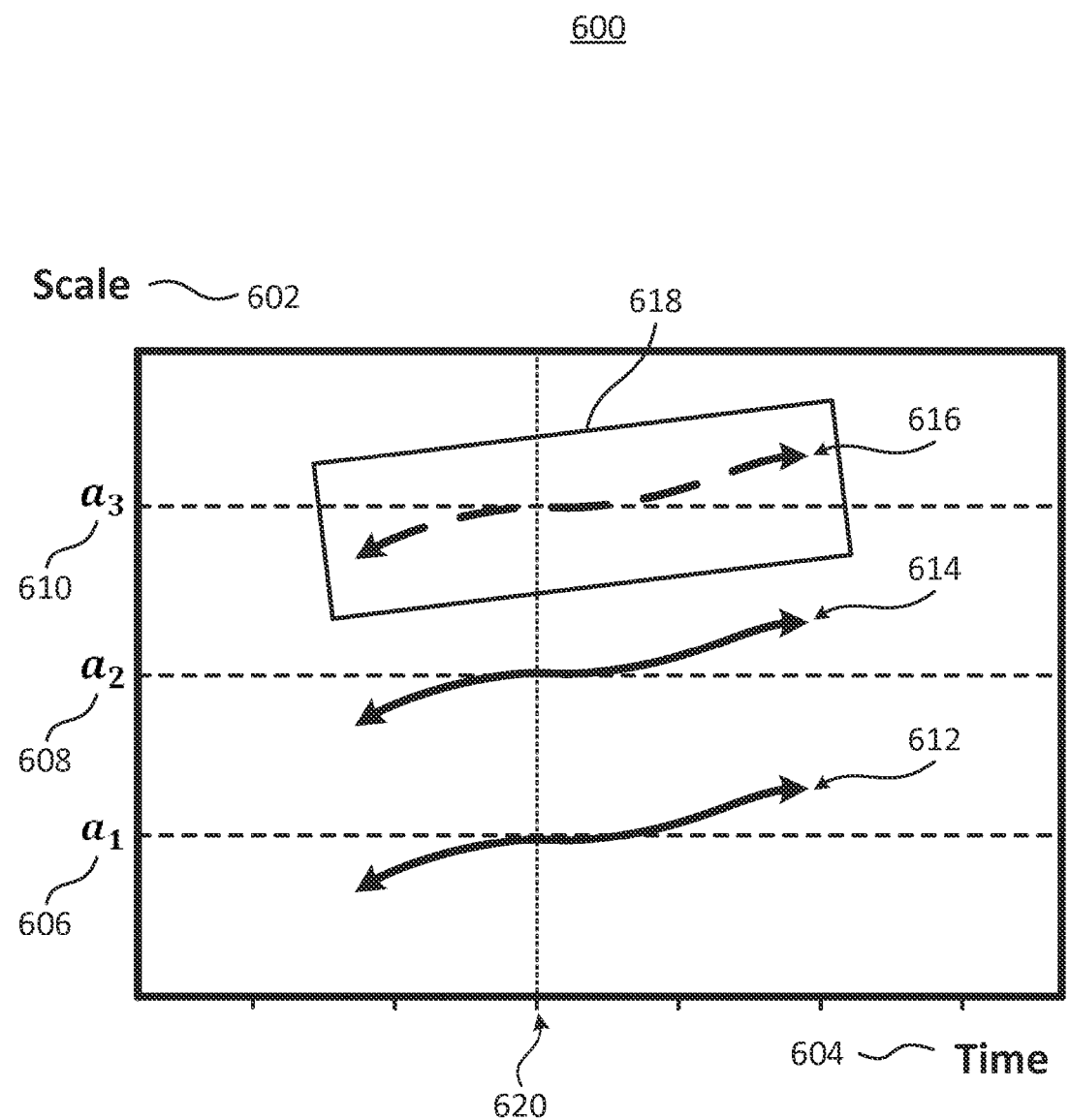
FIG. 6 is an illustrative plot for identifying coupled ridge pairs in accordance with some embodiments of the present disclosure.

As discussed above, in order to determine the non-stationary relationship parameter values (e.g., the NSBic and NSB given by Eqs. 8 and 9, respectively), the processing equipment must identify coupled ridge pairs along which to integrate and/or sum over time. FIGS. 4-6, described below, show illustrative plots for identifying coupled ridge pairs and/or determining whether pairs of ridges are coupled.

FIG. 4 is an illustrative plot 400 for identifying coupled ridge pairs in accordance with some embodiments of the present disclosure. Vertical axis 402 of plot 400 corresponds to a-scales and horizontal axis 404 corresponds to time. Plot 400 depicts ridges 412, 414, and 416. These are shown to cross scales local to them, $a_1$ 406, $a_2$ 408, and $a_3$ 410, respectively, where each is depicted as a dashed line.

In some embodiments, the processing equipment may identify ridges of the physiological signal in the transform domain. In some embodiments, the processing equipment may identify certain significant ridges in the wavelet transform domain, including for example, dominant ridges, ridges of features of interest, ridges of interest, ridges at scales of interest, ridges at bands of interest, ridges designated as significant based on user input, any other suitable subset of ridges in the wavelet transform, or any combination thereof. In some embodiments, the processing equipment analyzes each ridge triplet ($R_1$, $R_2$, $R_3$) to determine whether the ridges are related (e.g., form coupled ridge pairs). In some embodiments, the processing equipment determines if identified ridges 412, 414, and 416 are coupled ridges based on the scales at which ridges 412, 414, and 416 are located. For example, plot 400 includes ridges 412, 414, and 416, which pass, respectively, through scales $a_1$ 406, $a_2$ 408, and $a_3$ 410 at time 418. Scales $a_1$ 406, $a_2$ 408, and $a_3$ 410 form the triplet $(a_1, a_2, a_3)$. The processing equipment may determine that ridges 412, 414, and 416 are coupled if the corresponding triplet $(a_1, a_2, a_3)$ satisfies Eq. 1, above. It will be understood that ridges 412, 414, and 416 may vary in scale over time and that scale triplets may be analyzed over the length of the ridges over time. For example, at a given time, portions of ridges 412, 414, and 416 may be located respectively at scales $a_4$, $a_5$, and $a_6$, not shown, and the processing equipment may determine that ridges 412, 414, and 416 are coupled if the corresponding triplet $(a_4, a_5, a_6)$ satisfies Eq. 1. That is, in order for ridges 412, 414, and 416 to be coupled at this given time, it must be true or approximately true that:

$$\frac{1}{a_4} + \frac{1}{a_5} = \frac{1}{a_6} \quad [10]$$

In some embodiments, the processing equipment may identify coupled ridge pairs by identifying ridges of the physiological signal in the transform domain and generating all possible pairings of identified ridges (e.g., for 6 identified ridges, 15 unique pairs of identified ridges may be generated). The processing equipment may determine whether each of the pairings of ridges forms a coupled ridge pair. For example, the processing equipment may identify coupled ridge pairs based on the ridge amplitudes. The processing equipment may compute the amplitude of each ridge and compare the amplitudes of paired ridges to determine whether there is a relationship between the ridges.

FIG. 5 is an illustrative plot 500 for identifying coupled ridge pairs in accordance with some embodiments of the present disclosure. Vertical axis 502 of plot 500 corresponds to a-scales and horizontal axis 504 corresponds to time. Plot 500 depicts ridges 512, 514, and 516, which pass, respectively, through scales $a_1$ 506, $a_2$ 508, and $a_3$ 510 at time 524. Regions 518, 520, and 522 are shown as extending a predetermined amount above and below respective ridges 512, 514, and 516.

In some embodiments, the processing equipment may identify coupled ridge pairs based on regions 518, 520, and 522 in which part of each of ridges 512, 514, and 516 is respectively located. The processing equipment may identify ridges 512, 514, and 516 and analyze respective regions 518, 520, and 522 around each ridge to determine whether any of ridges 512, 514, and 516 are coupled. For example, the energies within regions 518, 520, and 522 may each be summed to determine absolute energies around each of the respective ridges 512, 514, and 516. The absolute energy values may be indicative of the strength of the feature of each of the ridges 512, 514, and 516. In some embodiments, the processing equipment may identify coupled ridge pairs based on the determined strength of the features. For example, the processing equipment may compare the determined strength of the features to determine whether there is a relationship between the respective ridges 512, 514, and 516.

FIG. 6 is an illustrative plot 600 for identifying coupled ridge pairs in accordance with some embodiments of the present disclosure. Vertical axis 602 of plot 600 corresponds to a-scales and horizontal axis 604 corresponds to time. Plot 600 depicts ridges 612 and 614 and suspected ridge 616, passing through respective scales $a_1$ 606, $a_2$ 608, and $a_3$ 610, which are each depicted as a dashed line. Suspected ridge 616 is shown as a dashed line inside region 618.

In some embodiments, the processing equipment may identify coupled ridge pairs based on region 618 of suspected ridge 616. Ridges 612 and 614 of plot 600 correspond, respectively, to time-varying features $F_1$ and $F_2$ of the transformed signal. In the embodiment shown, ridges 612 and 614 pass, respectively, through scales $a_1$ 606 and $a_2$ 608 at time 620. Ridges 612 and 614 vary in scale over time, and, thus, corresponding features $F_1$ and $F_2$ vary in scale over time. Because scales $a_1$ and $a_2$ are known, the processing equipment may determine scale $a_3$, which is related to scales $a_1$ and $a_2$ by Eq. 1. Thus, at time 620, a coupled ridge may pass through scale $a_3$. In some embodiments, the processing equipment may identify suspected ridge 616 by repeating this process for all scales through which ridges 612 and 614 respectively pass over a period of time to determine the scales through which suspected ridge 616 is expected to pass over the same period of time. For example, at a second time, ridges 612 and 614 may pass, respectively, through scales $a_4$ and $a_5$, and the processing equipment may determine scale $a_6$, which is related to scales $a_4$ and $a_5$ by Eq. 10, and through which suspected ridge 616 is expected to pass at the second time. In some embodiments, the processing equipment may analyze a region 618 around suspected ridge 616 in order to identify coupled ridges/features. For example, the processing equipment may search for a coupled feature $F_3$ corresponding to suspected ridge 616 within region 618.

It will be understood that the foregoing techniques described with reference to FIGS. 4-6 for identifying coupled ridge pairs are merely illustrative and are not presented by way of limitation. Any suitable technique for identifying a relationship or coupling between ridges, features, and/or scales may be used to identify coupled ridge pairs.

Figure 7:
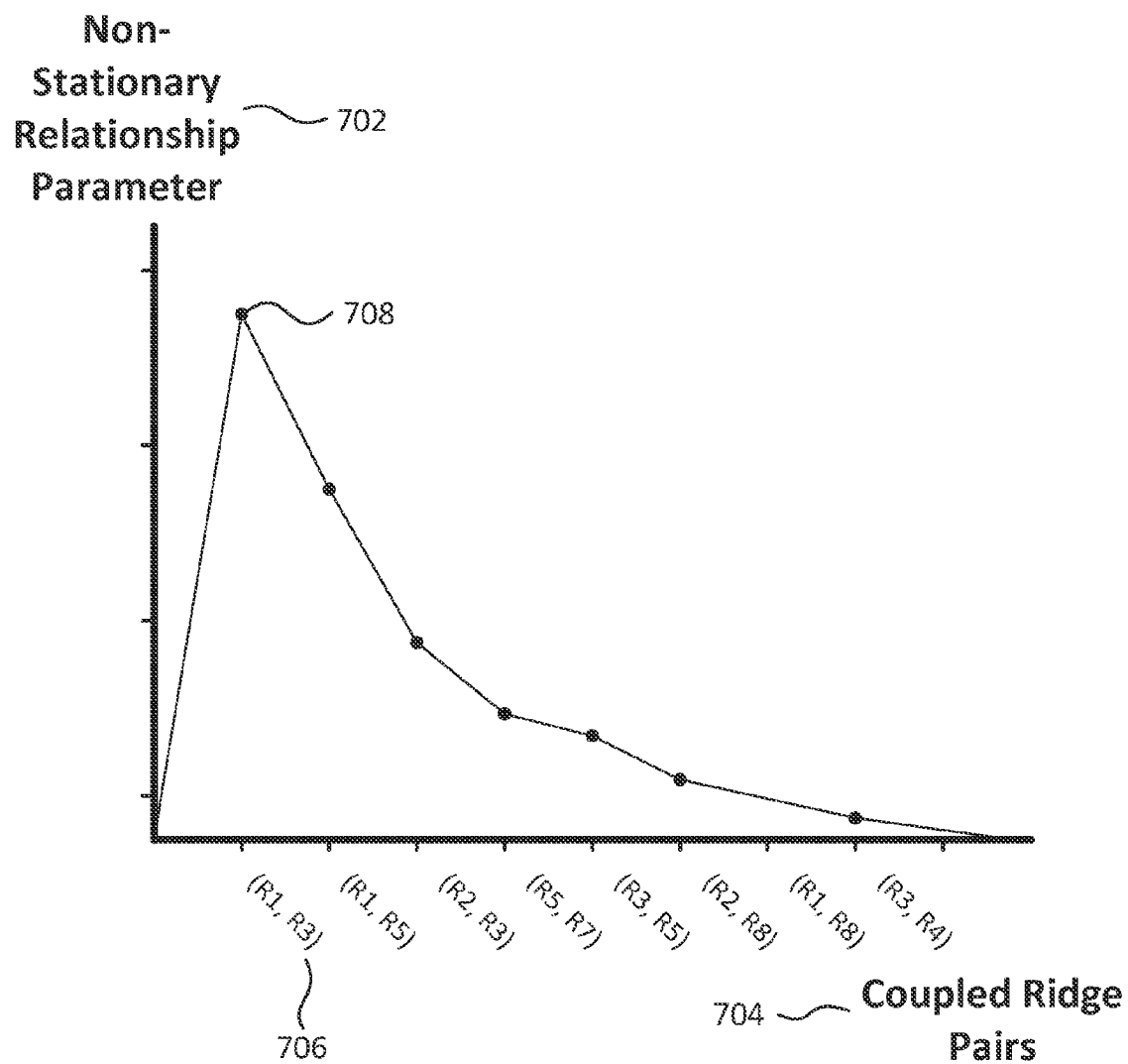
FIG. 7 is an illustrative plot of non-stationary relationship parameter values and corresponding coupled ridge pairs in accordance with some embodiments of the present disclosure.

FIG. 7 is an illustrative plot 700 of non-stationary relationship parameter values and corresponding coupled ridge pairs in accordance with some embodiments of the present disclosure. Vertical axis 702 of plot 700 corresponds to values of a non-stationary relationship parameter and horizontal axis 704 corresponds to coupled ridge pairs, each denoted $(R_i, R_j)$, where $i \ne j$, $i, j \in [1, n]$ for $\{n \in \mathbb{Z}^+ | n \ge 2\}$. It will be understood that $\mathbb{Z}^+$ denotes the set of positive integers and n is the number of identified ridges in the transformed signal. Plot 700 includes points marking the determined value of the non-stationary relationship parameter for each coupled ridge pair $(R_i, R_j)$. Point 708 indicates the largest value of the non-stationary relationship parameter, which corresponds to coupled ridge pair 706.

In some embodiments, the processing equipment includes a display for presenting the determined non-stationary relationship parameter values and corresponding feature sets or ridge pairs. In some embodiments, the display may correspond to display 218 of FIG. 2 or displays 120 or 128 of FIG. 1. In the embodiment shown, plot 700 shows plotted points corresponding to the non-stationary relationship parameter values (presented on vertical axis 702) for each coupled ridge pair $(R_i, R_j)$ (presented on horizontal axis 704). In some embodiments, the processing equipment may rank (e.g., from largest to smallest) the coupled ridge pairs based on the respective determined non-stationary relationship parameter values (e.g., NSBic values). In some embodiments, the coupled ridge pairs may be organized along horizontal axis 704 of plot 700 based on the ranking. In some embodiments, a coupled ridge pair may be selected based on the ranking. In the embodiment shown, the coupled ridge pairs are organized in descending order, with coupled ridge pair 706 ranking the highest as it corresponds to the largest determined non-stationary relationship parameter value indicated by point 708. In an example, coupled ridge pair 706 may be selected based on point 708, and the processing equipment may determine physiological information based on coupled ridge pair 706 and the corresponding non-stationary relationship parameter value indicated by point 708.

In some embodiments, the coupled ridge pairs and corresponding non-stationary relationship parameter values may be presented on a display in a histogram plot. In some embodiments, the coupled ridge pairs are organized in the histogram based on a ranking. In some embodiments, the physiological information may be determined based on the histogram. It will be understood that the foregoing techniques for displaying data are merely exemplary and not provided by way of limitation. It will also be understood that any suitable technique for presenting data on any suitable display may be used.

In some embodiments, the processing equipment may identify and determine the degree of related activity among signal components of the transformed signal based on the spectrum of ridge pair magnitudes shown in plot 700 of FIG. 7. For example, the processing equipment may select the coupled ridge pair corresponding to the largest non-stationary relationship parameter magnitude, the coupled ridge pairs corresponding to a preset number of largest magnitudes, or all the coupled ridge pairs corresponding to magnitudes above a predetermined threshold. The ridge coupled pairs may be selected within a wide band of scales corresponding to a physiological area of interest, for example, the alpha range, beta range, delta range, or theta range. In some embodiments, the presets and predetermined thresholds may be set based on user input. User input may be entered using, for example, user input 222 of FIG. 2. In some embodiments, the processing equipment may determine physiological information for a subject based on the one or more selected coupled ridge pairs. For example, the processing equipment may select the coupled ridge pair corresponding to the largest non-stationary relationship parameter (e.g., a high NSBic value), and the processing equipment may determine physiological information based on the NSBic. A high NSBic value may be attributed to strong phase coupling between the ridges or features, and this degree of linked brain activity may be indicative of subject awareness. In some embodiments, the NSBic value may be determined prior to the patient loosing awareness and this level, or a multiple of it (e.g., 80%) may be used as a threshold. In some embodiments, the physiological information may be indicative of a degree and/or quantity of related activity among signal components of the transformed signal. The related activity of signal components may be useful in determining a level of awareness of the subject, because a high degree and/or quantity of related activity may be indicative of linked brain activity and subject awareness. As described above, a relationship between ridges, features, and/or scales (i.e., related activity of signal components), may include, for example, phase coupling, grouping, similar characteristic shapes, signature patterns, any other morphology characteristic, any other determinable relationship, or any combination thereof.

Figure 8:
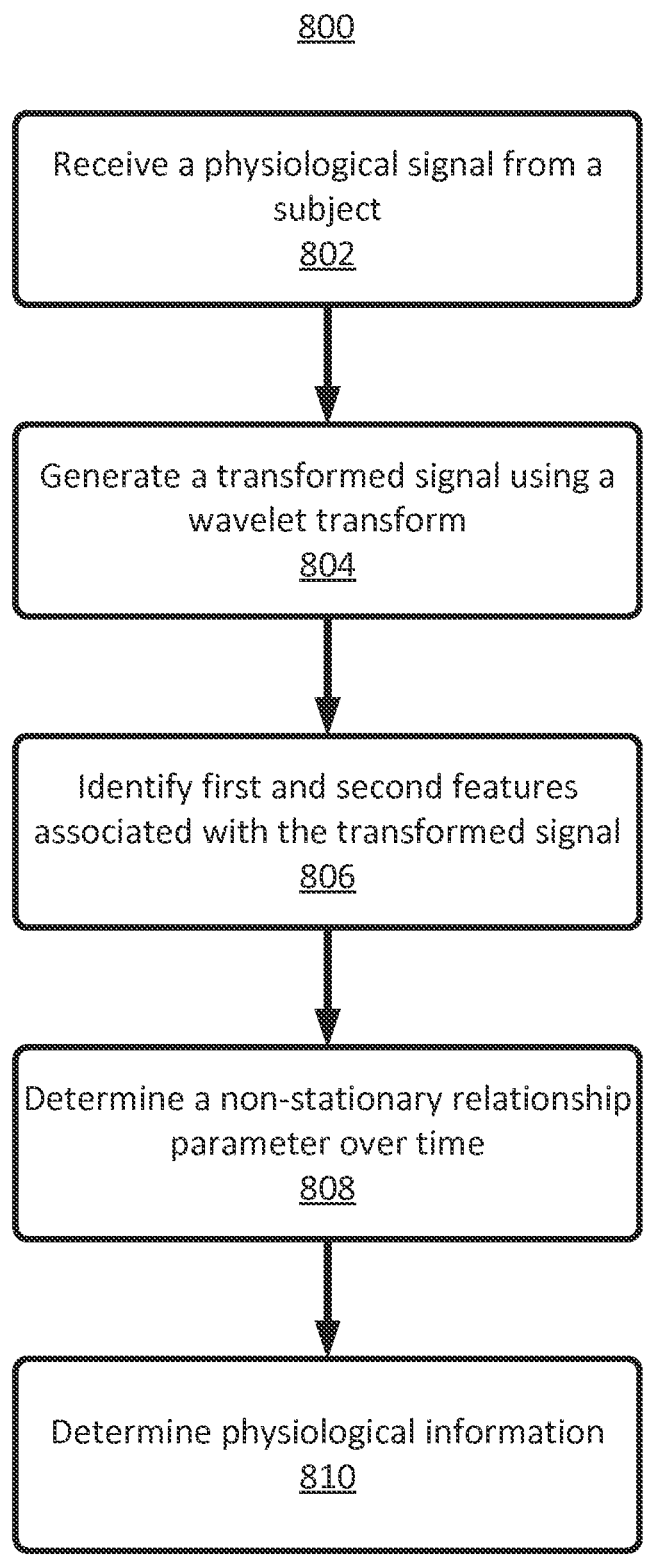
FIG. 8 shows an illustrative flow diagram including steps for determining physiological information in accordance with some embodiments of the present disclosure.

FIG. 8 shows an illustrative flow diagram 800 including steps for determining physiological information in accordance with some embodiments of the present disclosure.

At step 802, the processing equipment may receive a physiological signal (e.g., an EEG signal) from a subject. In some embodiments, a monitor, such as monitor 114 or 126 of FIG. 1, or processing circuitry, such as processor module 206 or processor 216 of FIG. 2, may receive the physiological signal. In some embodiments, the received physiological signal may have undergone signal processing before being received, such as any suitable band-pass filtering, adaptive filtering, closed-loop filtering, any other suitable filtering, or any combination thereof. In some embodiments, signal processing may be performed on the physiological signal after it has been received. It will be understood that the processing equipment may receive any suitable physiological signal. It will be understood that the received physiological signal is not limited to an EEG signal and may correspond to any suitable physiological signal, including, for example, including, for example, EMG signals, ECG signals, EGG signals, PPG signals, optical light signals, pulse rate signals, pathological signals, ultrasound signals, pressure signals, impedance signals, temperature signals, acoustic signals, any other suitable electrophysiological signals, any other suitable biosignals, or any combination thereof.

At step 804, the processing equipment may generate a transformed signal using a wavelet transform. In some embodiments, the processing equipment may generate a transformed signal using a continuous wavelet transform. It will be understood that the transformed signal is not limited to a wavelet transformed signal and may correspond to any transformed signal generated using any other suitable transform, including, for example, other time-scale and time-frequency transforms, or any combination thereof. In some embodiments, the transformed signal includes at least time and scale components. It will be understood that the transformed signal may correspond to any transformed signal, transformation of a transformed signal, rescaled version of a transformed signal, modulus of a transformed signal, phase of a transformed signal, squared magnitude of a transformed signal, any other suitable signal resulting from further signal processing or manipulation of the transformed signal, or any combination thereof.

At step 806, the processing equipment may identify first and second features associated with the transformed signal. In some embodiments, the processing equipment identifies a first feature associated with the transformed signal that varies in scale over time and a second feature associated with the transformed signal that varies in scale over time, where the first feature and the second feature are related (e.g., exhibit phase coupling). In some embodiments, the processing equipment identifies a first ridge corresponding to the first feature and a second ridge corresponding to the second feature, where the first ridge and the second ridge are coupled ridges (e.g., a coupled ridge pair). In some embodiments, the processing equipment may identify a plurality of ridges in the transformed signal and identify one or more coupled ridge pairs (i.e., first and second coupled ridges) in the plurality of ridges. As described above with respect to FIGS. 4-6, the processing equipment may identify the coupled ridge pairs using any suitable technique for identifying a relationship between ridges, features, and/or scales. A relationship between ridges, features, and/or scales, as used herein, includes, for example, phase coupling, grouping, similar characteristic shapes, signature patterns, any other morphology characteristic, any other determinable relationship, or any combination thereof.

At step 808, the processing equipment may determine a non-stationary relationship parameter over time. In some embodiments, the processing equipment may determine more than one non-stationary relationship parameter over time. Non-stationary relationship parameters may include, for example, bicoherence and bispectrum measures, any other suitable measures computed under a bispectral analysis, any suitable measures computed under a trispectral analysis, or any other suitable non-stationary measures indicative of a relationship between ridges, features, and/or scales. In some embodiments, the processing equipment may compute a first value of a non-stationary relationship parameter over a first period of time and a second value of the non-stationary relationship parameter over a second period of time. In some embodiments, the processing equipment may determine a non-stationary relationship parameter over time based on the identified first and second features and a third or higher order statistical equation (e.g., Eqs. 5 and 7 for instantaneous non-stationary bispectral analysis). In some embodiments, the processing equipment may determine a non-stationary relationship parameter over time based on the identified first and second ridges, as described above in step 806, and a third or higher order statistical equation (e.g., Eqs. 8 and 9 for non-stationary bispectral analysis).

At step 810, the processing equipment may determine physiological information. In some embodiments, the processing equipment may determine physiological information based on the non-stationary relationship parameter. In some embodiments, the processing equipment determines the physiological information based at least in part on one or more values of one or more non-stationary relationship parameters. In some embodiments, the processing equipment determines physiological information by comparing first and second computed values of a non-stationary relationship parameter, where the first and second values are computed over first and second periods of time, to determine a measure of coherence of the first and second features over time. In some embodiments, the physiological information is indicative of a level of awareness of a subject. It will be understood that level of awareness, as used herein, includes any measure indicative of a depth of consciousness, depth of sedateness, depth of anesthesia, awareness, any other suitable measure indicative of the subject's level of awareness, or any combination thereof. In some embodiments, the physiological information determined is a BIS index value.

In some embodiments, the processing equipment may determine one or more non-stationary awareness parameters based on the non-stationary relationship parameter. In some embodiments, the physiological information may correspond to a non-stationary version of a known stationary awareness parameter. For example, determining physiological information may include computing a non-stationary Synch-Fast-Slow parameter (NS_SynchFastSlow). In some embodiments, the non-stationary Synch-Fast-Slow parameter may be given by:

$$\text{NS\_SynchFastSlow} = \log\left(\frac{NSB_{x_1-x_2}^W}{NSB_{x_3-x_4}^W}\right) \quad [11]$$

where $NSB_{x_1-x_2}^W$ represents the non-stationary bispectrum values (e.g., NSB calculated with Eq. 9) associated with those one or more ridges that lie within the ranges of a-scales being considered (e.g., between $a=x_1$ and $a=x_2$). In some embodiments, the non-stationary bispectrum values to be used in Eq. 11 may be associated with one or more ridges outside a band of interest if any part of the ridges were within the band of interest at some point in time. In some embodiments, the processing equipment may disregard an entire ridge if, at some point in time, any part of the ridge falls outside the band of interest, and thus non-stationary bispectrum values may not be computed for disregarded ridges. In some embodiments, the processing equipment may compute non-stationary bispectrum values for a subset of the one or more ridges that appear in one or more bands of interest, for example, the dominant ridge or one or more ridges at the largest scales, or any other suitable subset of ridges. The processing equipment may compute the NS_SynchFastSlow parameter using non-stationary bispectrum values computed using any of the foregoing techniques. Hence NS_SynchFastSlow may be advantageous over stationary Synch-Fast-Slow measures as the processing equipment may filter out unwanted signal information during computation of the NS_SynchFastSlow parameter. In some embodiments, the processing equipment may select first and second coupled ridges (i.e., a coupled ridge pair) and compute the NS_SynchFastSlow parameter for these two ridges only. In some embodiments, the processing equipment may compute the NS_SynchFastSlow parameter based on user input. User input may be entered using, for example, user input device 222 of FIG. 2. User input may include, for example, identification of ridges, scales, or bands of interest, selection of a subset of one of more ridges, pre-set criteria for ridges to be used in the computation, selection of unwanted signal information to be filtered out, any other suitable selection or de-selection of ridges or signal components to be used in the parameter computation, or any combination thereof.

For purposes of brevity and clarity, and not by way of limitation, some examples in the foregoing discussion of flow diagram 800 were explained with the physiological information indicative of a level of awareness of a subject derived from an EEG signal. It will be understood that determining physiological information is not limited to determining a level of awareness based on an EEG signal and may correspond to any suitable physiological analysis based on any suitable physiological signal, or any combination thereof. In some embodiments, determining physiological information may correspond to arousal/sedateness monitoring and/or determining other HOS measures (e.g., measures computed under a trispectral analysis) based on any suitable signal (e.g., an EEG signal, PPG signal, and/or EMG signal). In some embodiments, determining physiological information may correspond to analyzing evoked and event related potentials based on EEG signal waveform components and/or analyzing EEG waveform components associated with epileptic seizures.

In some embodiments, the processing equipment may determine physiological information based on additional information. In some embodiments, the processing equipment may additionally determine second order statistical measures (e.g., power spectrum) based on the transformed signal. In some embodiments, the processing equipment may determine physiological information based on characteristics of identified features in the transform plane that are indicative of a level of awareness of the subject. These characteristics may be based on amplitude over time and/or scale, the spread, the number of features at a given time, the relationship between features (e.g., phase coupling, grouping, similar characteristic shapes, and/or signature patterns), the behavior of the ridges of the features, the modulus maxima associated with the features, any other suitable attributes of the features, or based on any combination thereof. In some embodiments, the characteristics may be indicative of physiological events occurring pre, onset, during, and/or post anesthesia.

In some embodiments, the processing equipment may determine HOS measures based on two or more transformed physiological signals. In some embodiments, the processing equipment may determine the cross-bicoherence based on two or more transformed physiological signals. For example, the cross-bicoherence may be determined based on two or more transformed EEG signals or one or more transformed EEG signals and one or more other transformed physiological signals. In another example, the cross-bicoherence may be determined based on a transformed EEG signal and a transformed PPG signal. In another example, the cross-bicoherence may be determined based on a transformed EEG signal and a transformed signal derived from a PPG signal (e.g., respiration rate, respiration effort, heart rate, $SpO_2$). In this case the determination of a triplet at a3 could be made from the EEG transform value of the EEG at scale a1 and the transform value of the pleth at scale a2. The triple at a3 could be located either in the transform of the EEG or the transform of the pleth, or both.

In some embodiments, determining physiological information may include determining a wavelet beta ratio (wβ-ratio) based on the power spectrum of the wavelet transformed signal. In some embodiments, we may define a wavelet spectrum as:

$$P^w(a) = \frac{1}{C}\int_\tau T(a_1, b)T^*(a_2, b)db \quad [12]$$

where C is a constant which may include a time period and the admissibility constant which depends on the wavelet used. We may further define the wβ-ratio as:

$$w\beta\_\text{Ratio} = \log\left(\frac{P_{x_1-x_2}^W}{P_{x_3-x_4}^W}\right) \qquad [13]$$

where $P_{x_1-x_2}^W$ represents the wavelet power spectrum values (e.g., $P^W(a)$ calculated with Eq. 12) associated values of the transform that lie within the ranges of a-scales being considered (e.g., between $a=x_1$ and $a=x_2$). In some embodiments, the beta ratio (β-ratio) may be defined as the logarithm of a ratio of powers from different regions of the power spectrum of a transformed signal. While the β-ratio may be indicative of a depth of consciousness of a subject, it is susceptible to corruption by transient noise and artifact. The wβ-ratio may provide a more accurate and de-noised value, because it is computed based on the power spectrum of a wavelet transformed signal, and the time-scale resolution of the wavelet transform may be used to remove transient noise and artifact. For example, in a wavelet transformed signal, a ridge may be tracked through time to determine its validity, modulus maxima techniques may be used to remove transient noise, resulting in de-noised, wavelet transformed signal. In the example, the processing equipment may determine a wβ-ratio based on the de-noised, wavelet transformed signal by, for example, integrating across first and second selected regions of a power scalogram generated from the de-noised, wavelet transformed signal, normalizing the integral of a first selected region by the integral of a second selected region, and then taking the logarithm to compute the wβ-ratio. The wβ-ratio may be indicative of a depth of consciousness of the subject.

It will be understood that the steps above are exemplary and that in some implementations, steps may be added, removed, omitted, repeated, reordered, modified in any other suitable way, or any combination thereof.

The foregoing is merely illustrative of the principles of this disclosure, and various modifications may be made by those skilled in the art without departing from the scope of this disclosure. The above-described embodiments are presented for purposes of illustration and not of limitation. The present disclosure also can take many forms other than those explicitly described herein. Accordingly, it is emphasized that this disclosure is not limited to the explicitly disclosed methods, systems, and apparatuses, but is intended to include variations to and modifications thereof, which are within the spirit of the following claims.

What is claimed:

1. A system for determining awareness information comprising:
    an input configured for receiving an electrophysiological signal from an electrode attached to a subject;
    a display; and
    one or more processors configured for:
        transforming the electrophysiological signal based on a wavelet transform to generate a non-stationary transformed signal that comprises at least a time component and a scale component;
        identifying a first ridge in the non-stationary transformed signal that varies in scale over time;
        identifying a second ridge in the non-stationary transformed signal that varies in scale over time, wherein the first ridge is related to the second ridge;
        determining a non-stationary relationship parameter over time based on a third or higher order spectral analysis, the first ridge, and the second ridge, wherein the non-stationary relationship parameter is indicative of the relationship between the first ridge and the second ridge;
        determining a level of awareness of the subject based on the non-stationary relationship parameter; and
        presenting information, via the display, regarding the determined level of awareness.

2. The system of claim 1, wherein:
    determining a non-stationary relationship parameter over time comprises:
        computing a first value of the non-stationary relationship parameter over a first period of time, and
        computing a second value of the non-stationary relationship parameter over a second period of time; and
    determining a level of awareness comprises comparing the computed first and second values of the non-stationary relationship parameter to determine a measure of coherence of the first and second ridges over time.

3. The system of claim 1, wherein the one or more processors are further configured for identifying a band of interest in the non-stationary transformed signal, and wherein identifying a first ridge is based on the band of interest.

4. The system of claim 1, wherein the one or more processors are further configured for:
    determining suspected scales over a period of time based on the scale of the first ridge and the scale of the second ridge over the same time period, and
    identifying a third ridge associated with the non-stationary transformed signal that varies in scale over time based on a region containing the suspected scales.

5. The system of claim 1, wherein the one or more processors are further configured for:
    identifying a plurality of ridges in the non-stationary transformed signal, wherein the plurality of ridges comprises the first ridge and the second ridge;
    identifying a plurality of coupled ridge pairs in the plurality of ridges, wherein each of the plurality of coupled ridge pairs comprises respective first and second coupled ridges; and
    determining a value of the non-stationary relationship parameter over time, for each of the plurality of coupled ridge pairs, based on a third or higher order spectral analysis and the respective first and second coupled ridges.

6. The system of claim 5, wherein the one or more processors are further configured for computing a plurality of energy values, wherein each of the plurality of energy values is based on one of the plurality of ridges; and wherein identifying a first ridge is based on the plurality of energy values.

7. The system of claim 5, wherein determining a level of awareness comprises:
    determining a first value of the non-stationary relationship parameter based on a first coupled ridge pair of interest in the plurality of coupled ridge pairs;
    determining a second value of the non-stationary relationship parameter based on a second coupled ridge pair of interest in the plurality of coupled ridge pairs; and
    determining an awareness parameter based on a ratio of the first and second values of the non-stationary relationship parameter, wherein the awareness parameter is indicative of a depth of anesthesia of the subject.

8. The system of claim 5, wherein the one or more processors are further configured for:
ranking the plurality of coupled ridge pairs based on the respective determined non-stationary relationship parameter values;
selecting one or more of the coupled ridge pairs based on the ranking; and
determining awareness information based on the selected one or more coupled ridge pairs.

9. The system of claim 8, wherein the one or more processors are further configured for generating a histogram of the plurality of coupled ridge pairs and the respective determined non-stationary relationship parameter values, wherein the plurality of coupled ridge pairs are ordered based on the ranking, and wherein the awareness information is determined based on the histogram.

10. The system of claim 9, wherein determining awareness information comprises:
identifying, based on the histogram, one or more coupled ridge pairs with respective determined non-stationary relationship parameter values that exceed a threshold; and
determining awareness information based on the identified one or more coupled ridge pairs.

11. The system of claim 1, wherein the one or more processors are further configured for determining a ratio of powers from a first region and a second region of a power spectrum, wherein the power spectrum is determined based on the non-stationary transformed signal, and wherein the ratio is indicative of a level of awareness of the subject.

12. The system of claim 1, wherein the electrophysiological signal is an electroencephalogram EEG signal.

13. The system of claim 1, wherein the third or higher order spectral analysis comprises a bispectral analysis.

14. A method for determining awareness information comprising:
receiving from an input an electrophysiological signal from an electrode attached to a subject;
transforming, using one or more processors, the electrophysiological signal based on a wavelet transform to generate a non-stationary transformed signal that comprises at least a time component and a scale component;
identifying, using one or more processors, a first ridge in the non-stationary transformed signal that varies in scale over time;
identifying, using one or more processors, a second ridge in the non-stationary transformed signal that varies in scale over time, wherein the first ridge is related to the second ridge;
determining, using one or more processors, a non-stationary relationship parameter over time based on a third or higher order spectral analysis, the first ridge, and the second ridge, wherein the non-stationary relationship parameter is indicative of the relationship between the first ridge and the second ridge;
determining, using one or more processors, a level of awareness of the subject based on the non-stationary relationship parameter; and
displaying, via a display, information regarding the determined level of awareness.

15. The method of claim 14, wherein:
determining a non-stationary relationship parameter over time comprises:
computing a first value of the non-stationary relationship parameter over a first period of time, and
computing a second value of the non-stationary relationship parameter over a second period of time; and
determining a level of awareness comprises comparing the computed first and second values of the non-stationary relationship parameter to determine a measure of coherence of the first and second ridges over time.

16. The method of claim 14, further comprising identifying a band of interest in the non-stationary transformed signal, and wherein identifying a first ridge is based on the band of interest.

17. The method of claim 14, further comprising:
identifying, using one or more processors, a plurality of ridges in the non-stationary transformed signal, wherein the plurality of ridges comprises the first ridge and the second ridge;
identifying, using one or more processors, a plurality of coupled ridge pairs in the plurality of ridges, wherein each of the plurality of coupled ridge pairs comprises respective first and second coupled ridges; and
determining, using one or more processors, a value of the non-stationary relationship parameter over time, for each of the plurality of coupled ridge pairs, based on a third or higher order spectral analysis and the respective first and second coupled ridges.

* * * * *